United States Patent [19]

Stone

[11] Patent Number: 5,116,374
[45] Date of Patent: May 26, 1992

[54] PROSTHETIC MENISCUS

[75] Inventor: Kevin R. Stone, San Francisco, Calif.

[73] Assignee: ReGen Corporation, San Francisco, Calif.

[21] Appl. No.: 582,516

[22] Filed: Sep. 13, 1990

Related U.S. Application Data

[60] Division of Ser. No. 317,951, Mar. 2, 1989, Pat. No. 5,007,934, which is a continuation-in-part of Ser. No. 75,352, Jul. 20, 1987, Pat. No. 4,880,429.

[51] Int. Cl.⁵ .............................................. A61F 2/20
[52] U.S. Cl. .................................................. 623/16
[58] Field of Search ................ 623/11, 12, 16, 18, 623/66, 20

[56] References Cited

U.S. PATENT DOCUMENTS

| | | |
|---|---|---|
| 3,443,261 | 5/1969 | Battista et al. ........................ 3/1 |
| 3,551,560 | 12/1970 | Thiele ................................ 424/95 |
| 3,855,638 | 12/1974 | Pilliar . |
| 4,000,525 | 1/1977 | Klawitter et al. . |
| 4,055,862 | 11/1977 | Farling ............................... 3/1.91 |
| 4,060,081 | 11/1977 | Yannas et al. ........................ 128/156 |
| 4,064,567 | 12/1977 | Burstein et al. ....................... 3/1.91 |
| 4,085,466 | 4/1978 | Goodfellow et al. .................. 3/1.91 |
| 4,280,954 | 7/1981 | Yannas et al. ........................ 260/123.7 |
| 4,291,013 | 9/1981 | Wahlig et al. ........................ 424/16 |
| 4,344,193 | 8/1982 | Kenny ................................ 3/1.911 |
| 4,350,629 | 9/1982 | Yannas et al. ........................ 260/123.7 |
| 4,351,069 | 9/1982 | Ballintyn et al. ..................... 3/1.912 |
| 4,378,224 | 3/1983 | Nimni et al. .......................... 8/94.11 |
| 4,385,404 | 5/1983 | Sully et al. ........................... 3/1.91 |
| 4,400,833 | 8/1983 | Kurland .............................. 3/1 |
| 4,418,691 | 12/1983 | Yannas et al. ........................ 128/156 |
| 4,448,718 | 5/1984 | Yannas et al. ........................ 260/123.7 |
| 4,458,678 | 7/1984 | Yannas et al. ........................ 128/155 |
| 4,472,840 | 9/1984 | Jefferies ............................. 3/1.9 |
| 4,502,161 | 3/1985 | Wall .................................. 3/1.91 |
| 4,505,266 | 3/1985 | Yannas et al. ........................ 128/1 R |
| 4,542,539 | 9/1985 | Rowe, Jr. et al. ..................... 623/16 |
| 4,544,516 | 10/1985 | Hughes et al. ....................... 264/108 |
| 4,578,079 | 3/1986 | Ruoslahti et al. ..................... 623/11 |
| 4,589,881 | 5/1986 | Pierschbacher et al. ............... 623/11 |
| 4,614,794 | 9/1986 | Easton et al. ........................ 530/536 |
| 4,627,853 | 12/1986 | Campbell et al. ..................... 623/16 |
| 4,661,111 | 4/1987 | Ruoslahti et al. ..................... 623/11 |

FOREIGN PATENT DOCUMENTS

0277678 10/1988 European Pat. Off. .

OTHER PUBLICATIONS

Smillie (May 1943) The British Journal of Surgery, Meeting of the British Orthopaedic Association pp. 398-401.
Bullough et al. (1970) J. Bone Joint Surg. 52B:564-570.
Cox and Cordell (1977) Clin. Orthopaed. Related Res. 125:236-242.
Seedham (1979) Engin. Med. 8:207-219.
Seedham and Hargreaves (1979) Engineering in Medicine IMechE 8:220-228.
Arnoczky and Warren (1983) J. Sports Med. 11:131-141.
Arnoczky *Advances in Orthopaedic Surgery*, copyright 1984 by the Williams and Wilkins Co pp. 244-252.
Anderson (1984) *Grant's Atlas of Anatomy* (8th Ed.) Williams and Wilkins, Baltimore/London, sections 4-56, 4-57, 4-60, and 4-61.

(List continued on next page.)

[57] ABSTRACT

A prosthetic, resorbable meniscus and method of its fabrication are disclosed. The prosthetic meniscus can be implanted in a human knee where it can act as a scaffold for regrowth of native meniscal tissues. The meniscus comprises a dry, porous, matrix of biocompatible and bioresorbable fibers, at least a portion of which may be crosslinked. The fibers include natural polymers or analogs or mixtures thereof. The matrix is adapted to have in vivo an outer surface contour substantially the same as that of a natural meniscus. The matrix has pore size in the approximate range of greater than 50 microns to less than about 500 microns. With this configuration, the matrix establishes an at least partially bioresorbable scaffold adapted for ingrowth of meniscal fibrochondrocytes.

5 Claims, 6 Drawing Sheets

OTHER PUBLICATIONS

Arnoczky et al. 32nd Annual ORS, New Orelenas, La., Feb. 17-20, 1986.

Leenslag et al. (1986) *Biological and Biomechanical Performance of Biomaterials* (Christel et al., eds.) Elsevier Science Publishers B.V., Amsterdam, (1986), pp. 147-152.

Milachowski et al. (1986) Orthopadischem Klinik, Klinikum Grosshadern, Munchen. z. Orhop. (Jul.-Aug. 1986) 124:508-512.

Ahmed (19) "Load-Carrying Characteristics of Meniscus and Tibial Plateau—a Review of Recent Results". Beaupré et al. (1986) Clin. Ortho. and Rel. Res. 208:72-75.

*Primary Examiner*—David J. Isabella
*Attorney, Agent, or Firm*—Lahive & Cockfield

PROSTHETIC MENISCUS

REFERENCE TO RELATED APPLICATION

This is a division of application Ser. No. 317,951, filed Mar. 2, 1989, now U.S. Pat. No. 5,007,934, which is a continuation-in-part of copending U.S. patent application Ser. No. 075,352, filed Jul. 20, 1987; now U.S. Pat. No. 4,880,429.

FIELD OF THE INVENTION

The present invention is in the field of implantable medical devices, and more particularly, is directed to devices useful as prosthetic menisci, and in vivo scaffolds for regeneration of meniscal tissue and to methods for their fabrication.

BACKGROUND OF THE DISCLOSURE

The medial and lateral menisci are a pair of cartilaginous structures in the knee joint which together act as a crucial stabilizer, a mechanism for force distribution, and a lubricant in the area of contact between the tibia and femur. Without the menisci, stress concentration occurs in the knee in conjunction with abnormal joint mechanics, and premature development of arthritic changes occurs.

In the prior art, treatment of injured or diseased menisci has generally been both by surgical repair and by excision. With excision, regeneration of meniscal tissue may occur. Additionally, it is known that meniscal fibrochondrocytes have the ability to migrate into a defect filled with a fibrin clot and form tissue apparently similar to normal meniscal fibrocartilage. When an adequate matrix scaffold is present within a meniscal defect, such meniscal fibrocartilage may be formed. Meniscal tissue is also capable of self-repair when exposed to bleeding tissues, and additionally, it is also known in the prior art that meniscal cells in tissue culture are capable of cell division and matrix synthesis. Replacement of an injured meniscus in an otherwise healthy joint may prevent arthritic changes and may stabilize the joint. In diseased joints, replacement of the meniscus may reduce the progression of the disease process, and may provide pain relief. Allografting or meniscal transplantation, is one method of replacement which has been executed both in dogs and in humans. However, this approach has been only partially successful over the long term due to the host's immunologic response to the graft, to failures in the cryopreservation process, and to failures of the attachment sites.

In alternative prior art replacement approaches, menisci have been replaced with prostheses composed of permanent artificial materials. Such prosthesis have been constructed of purely artificial materials in order to minimize the possibility of an immunological response. In addition, the use of such materials is believed to be advantageous because it permits construction of a structure which can withstand the high and repeated loads which are encountered in the knee joint, and because it can alter the joint mechanics in beneficial ways that biological materials would not tolerate.

For example, a Teflon net has been used to replace the resected meniscus of a dog upon which fibrous ingrowth or regeneration was observed, although accompanied by significant chondral abrasion. A prosthetic meniscus has also been constructed from resilient materials such as silicone rubber or Teflon with reinforcing materials of stainless steel or nylon strands (U.S. Pat. No. 4,502,161). A meniscal component has also been made from resilient plastic materials (U.S. Pat. No. 4,085,466). In addition, reconstruction of meniscal lesions has been attempted with carbon-fiber-polyurethane-poly (L-lactide), but its success with these materials is minimal (Leeslag et al., *Biological and Biomechanical Performance of Biomaterials* (Christel et al., eds.) Elsevier Science Publishers B.V., Amsterdam, 1986, pp: 347-352).

However, the replacement of meniscal tissue with structures consisting of permanent artificial materials generally has been unsuccessful, principally because the opposing articular cartilage of human and animal joints is fragile. The articular cartilage in the knee will not withstand abrasive interfaces, nor compliance variances from normal, which eventually results from the implantation of prior art artificial menisci. Additionally, joint forces are multiples of body weight which, in the case of the knee and hip, are typically encountered over a million cycles per year. Thus far, prior art permanent artificial menisci have not been composed of materials having natural meniscal properties, nor have they been able to be positioned securely enough to withstand such routine forces.

Therefore, what is needed is an improved prosthetic meniscus composed of biocompatible materials which are soft and lubricating.

Repair of other tissues such as skin and nerve has been attempted using both synthetic and natural materials. For example, Yannas et al., fashioned endodermal implants, and artificial epidermis out of natural collagen and glycosaminoglycans (U.S. Pat. No. 4,060,081). Nyiles et al. (Trans. Am. Soc. Artif. Intern. Organs (1983) 29:307-312) reported the use of synthetic resorbable polyesters for peripheral nerve regeneration applications, and the use of collagen conduits as a scaffold for nerve regeneration.

However, even with the foregoing technologies which have been applied to the reconstruction of anatomical structures other than knee joints, a structure suitable as a prosthetic meniscus and constructed from totally resorbable natural materials, or analogs thereof, has not been developed in the prior art.

Accordingly, it is an object of this invention to provide an improved meniscal prosthesis which allows for normal joint motion.

Another object is to provide a meniscal replacement or prosthesis which is biomechanically able to withstand normal joint forces and is able to function at those loads to protect the cartilage and stabilize the joint.

Yet another object is to provide a resorbable meniscal prosthesis which acts as a temporary in vivo scaffold for meniscal fibrocartilage infiltration and regeneration.

Still another object is to provide a meniscal prosthesis which is composed of biocompatible materials having an organization equivalent to that of the normal meniscus.

A further object is to provide a meniscal prosthesis which is adapted for implantation by standard operative techniques.

Another object is to provide a method of regenerating meniscal tissue in vivo.

Still a further object is to provide a method by which such prosthetic menisci can be fabricated.

SUMMARY OF THE INVENTION

The present invention provides a biocompatible and bioresorbable structure for implantation into the knee joint which assumes the form and role of a meniscus. This prosthetic meniscus promotes and provides a scaffold for the regeneration of tissue having the physical characteristics of a natural meniscus.

The prosthetic meniscus of the present invention is generally a dry, porous matrix of biocompatible bioresorbable fibers, including natural polymers or analogs or mixtures thereof. The matrix is adapted to have in vivo an outer surface contour substantially the same as that of a natural meniscus. Further, the matrix has pore size in the approximate range of greater than 50 microns to less than about 500 microns. With this configuration, the matrix establishes an at least partially bioresorbable scaffold adapted for ingrowth of meniscal fibrochondrocytes. The matrix may have the shape of a circumferentially extending wedge spanning a predetermined angle greater than 0 degrees, and less than or equal to 360 degrees, and having a thickness in its central region which is less than its thickness in its peripheral regions. In some forms of the invention, the matrix may assume the shape of a simple wedge, a crescent-shaped wedge with a wide central region between two narrow distal tip regions, or a circumferentially extending wedge spanning an angle of 360 degrees and having a depressed (concave) central region, for example.

The matrix is composed of biocompatible and bioresorbable fibers, a portion of which may be crosslinked. The fibers include a natural material or an analog of a natural material such as a biosynthetic analog. In a preferred embodiment of the invention, the fibers of the matrix are polymers of, for example, natural molecules such as those obtained from animal or human tissue. Natural fibers useful for the same purpose include collagen, elastin, reticulin, analogs thereof, and mixtures thereof.

In some forms of the invention, the fibers may be randomly orientated throughout the matrix, or may be ordered at specified regions. Alternatively, the fibers may assume substantially circumferentially extending or substantially radially extending orientations throughout the prosthetic meniscus.

The matrix may also include glycosaminoglycan molecules (GAGs) interspersed with the fibers. GAGs are any mucopolysaccharide molecules which provide lubrication and crosslinks for the prosthetic meniscus of the invention. In the preferred aspects of the invention, GAGs such as chondroitin 4-sulfate, chondroitin 6-sulfate, keratan sulfate, dermatan sulfate, heparin sulfate, hyaluronic acid, and mixtures thereof are a component of the matrix. These GAGs may be uniformly dispersed throughout the prosthetic meniscus as individual molecules, or may be present in varying amounts in different regions of the structure.

In various forms of the invention, GAGs may directly participate in covalent crosslinking formation with the fibers, or may interact with the fibers mechanically in the form of entanglement or through interlocking mechanisms, forming stable fiber-GAG complexes.

The matrix include about 75-100% natural and/or synthetic fibers and about 0-25% GAGs by dry weight, the proportions of which may be constant throughout the structure or may be variable.

In a preferred embodiment of the invention, the matrix has a density of about 0.07 to 0.50 g matrix/cm$^3$ where "g matrix/cm$^3$" is a unit connoting the number of grams in a cubic centimeter of the matrix. In addition, it has an interfibrillary and interfibrillary space of about 2 to 25 cm$^3$/g matrix.

In another form of the invention, the prosthetic meniscus may further comprise a mesh composed of a bioresorbable, biocompatible material which is attached to portions of the outer surface of the matrix. The mesh aids in the successful implantation of the prosthetic meniscus into the knee joint by providing a temporary anchoring mechanism.

The invention also includes a method of regenerating meniscal tissue in vivo. This method includes fabricating a prosthetic meniscus and implanting it into the knee joint by surgical procedures.

Further, the invention includes a method for fabricating a prosthetic meniscus of the type described above. Generally, the method includes placing a plurality of fibers and/or fibers and GAGs into a mold having a shape useful for knee joint function, subjecting the fibers (and GAGs) in the mold to two cycles of freezing and thawing, contacting said fibers or said fibers and GAGs with a chemical crosslinking reagent such that the fibers then assume the shape of the mold, and lyophilizing the resulting structure to obtain a dry, porous, volume matrix.

The fibers may be laid down in a circumferential orientation by rotating the mold as they are placed therein. Alternatively the fibers in the mold may be compressed with a rotating piston. Radial orientation of the fibers is produced by manually painting the fibers in a linear, radially directed fashion.

Specific densities and pore sizes may be obtained in various regions of the matrix by compressing the fibers or fibers and GAGs in the mold prior to the second freeze-thaw cycle, subsequent to the chemical crosslinking step. This may be accomplished by applying pressure to a specific region of the matrix with a piston of a predetermined shape.

In a preferred aspect of the invention, the crosslinking step is performed using chemical agents which form intramolecular and intermolecular crosslinks. Useful chemical agents include, for example, glutaraldehyde, formaldehyde, biocompatible bifunctional aldehydes, carbodiimides, hexamethylene diisocyanate, bis-ionidates, glyoxal, polyglycerol polyglycidyl ether, glyoxal, and mixtures thereof. Particularly useful crosslinking agents are 1-ethyl, 3-(3-dimethylaminopropyl), polyglycerol polyglycidyl ether and glutaraldehyde.

In other aspects of the invention, an additional crosslinking step is performed by lyophilizing the chemically crosslinked matrix and then subjecting it to dehydrothermal crosslinking procedures.

The invention will next be described in connection with certain illustrated embodiments. However, it should be clear that various modifications, additions, and deletions can be made without departing from the spirit or scope of the invention.

BRIEF DESCRIPTION OF THE DRAWINGS

The foregoing and other objects of this invention, the various features thereof, as well as the invention, itself, may be more fully understood from the following description, when read together with the accompanying drawings.

DESCRIPTION OF THE INVENTION

It has been discovered that a prosthetic meniscus fabricated from biocompatible and bioresorbable fibers can be surgically implanted into the knee joint so as to provide normal joint motion and strength. This prosthetic meniscus also acts as a scaffold for regenerating meniscal tissue whose ingrowth is encouraged by the physical characteristics of the implanted device.

Figure 1:
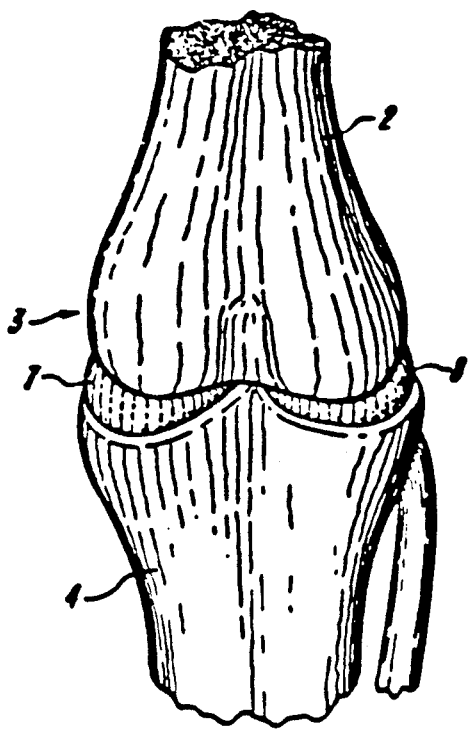
FIG. 1 shows a simplified diagramatic representation of a human knee joint, with menisci in native positioning.
Figure 1A:
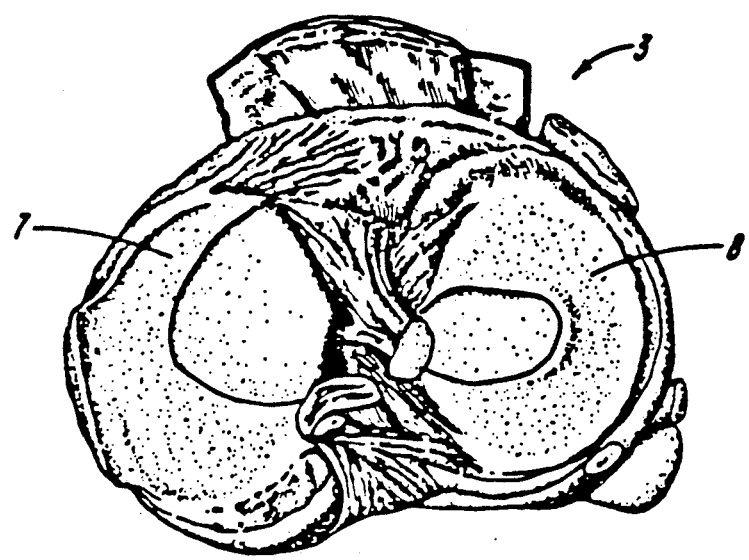
FIG. 1A is a diagrammatic representation of a cut-away view of the knee joint showing the medial and lateral menisci as they are positioned in vivo over the medial and lateral condyles.

FIG. 1 shows a diagramatic representation of the normal positioning of medial meniscus 7 and lateral meniscus 8 in the human knee joint 3 between the femur 2 and tibia 4. These menisci, when compressed between the femur 2 and tibia 4, become tough except at their points of attachment. FIG. 1A shows the in vivo structure of medial meniscus 7 and lateral meniscus 8 in the knee joint 3. The menisci conform to the shapes of the surfaces between which they are positioned, thereby resulting in two distinct in vivo forms. For example, the medial meniscus 7 has a relatively open crescent shape, while the lateral meniscus 8 has a relatively closed crescent shape.

Figure 2:
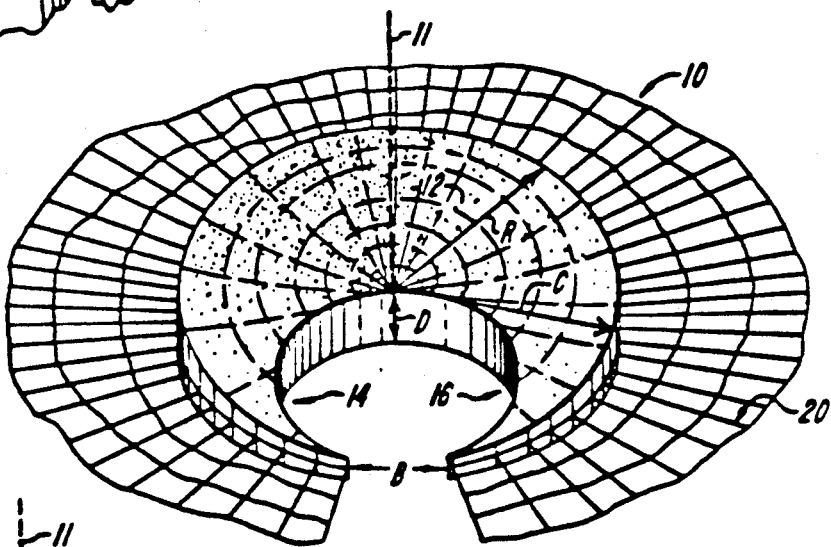
FIG. 2 shows a perspective view of an exemplary prosthetic meniscus in accordance with the present invention.

An exemplary prosthetic meniscus 10 is shown in FIG. 2. The prosthetic meniscus 10 is a generally wedge-shaped, porous dry matrix or scaffold which extends circumferentially or laterally at least in part about a central axis 11. In the preferred form, the prosthetic meniscus 10 has the shape of a crescent-shaped wedge, extending circumferentially about the axis 11, and comprising a relatively wide central region 12 between two narrow distal regions 14 and 16. In the preferred form, the wedge has maximum height A at its peripheral edge of approximately 0.4 inches, a height D at its central point of approximately 0.2 inches, and a maximum radial dimension C of approximately 1.0 inches. The cresent shaped wedge subtends an angle B about axis 11 substantially in the range of about 135 to about 155 degrees, and preferably of about 150 degrees.

In the embodiment illustrated in FIG. 2, the prosthetic meniscus 10 includes a mesh member 20 extending from its peripheral edge. The mesh member 20 is composed of a biocompatible, bioresorbable material, and provides a readily used means for anchoring the array 10 in place. The mesh member 20 may function in this capacity until sufficient tissue ingrowth occurs to then provide that function. By way of an example, the mesh member 20 may be a #1, mesh screen composed of absorbable suture materials such as polyglyconate, Dexon, or polydioxane (PDS) woven into a mesh. Nonabsorbable suture materials such as Goretex may also be used.

Figure 4:
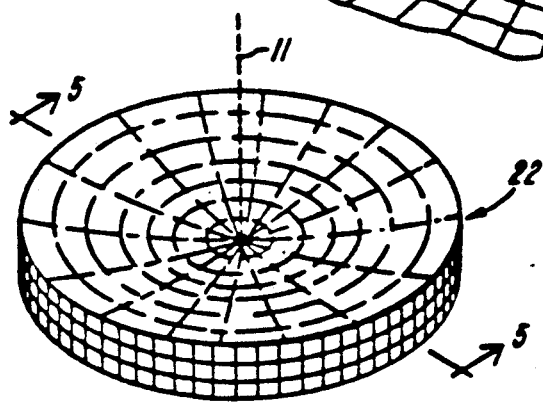
FIG. 4 shows a perspective view of an alternative embodiment of the present invention.
Figure 5:
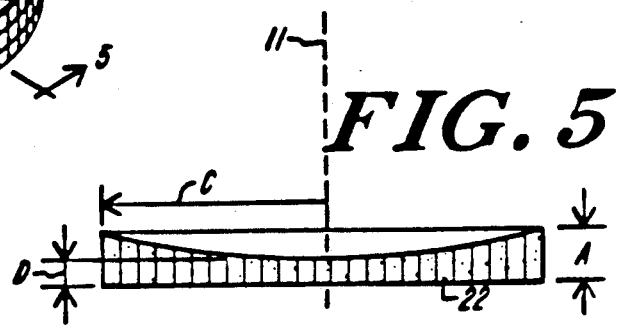
FIG. 5 shows a sectional view along line 5—5 of the prosthetic meniscus of FIG. 4.

FIGS. 4 and 5 show an additional embodiment of the present invention which is similar in composition to the prosthetic meniscus depicted in FIG. 2. More particularly, FIG. 4 depicts a right circular cylinder-shaped meniscus 22, extending fully about axis 11, i.e. where angle B equals 0 degrees. (i.e. the meniscus subtends 360 degrees.) FIG. 5 shows a sectional view along line 5—5 of the meniscus shown in FIG. 4. The device illustrated in FIGS. 4 and 5 show the shape of the meniscus 22 when implanted; that is, the height D at areas 11 is less than the peripheral height A of the device. Prior to implantation, the device 22 may in some cases not have this relationship but upon implantation, the normal loads applied by the body force this conformation.

In alternative forms of the invention, still other shapes may be used. For example, it is not required that the wedge be symmetrical. These embodiments may have densities of collagen fibers and dispersions of GAG molecules and crosslinks, permitting accommodation of differing stress levels, rates of ingrowth, and resiliency. Differing densities may be obtained in vivo where a device having uniform density is implanted, and body loading causes non-uniform compression of the device.

The prosthetic meniscus may be fabricated of any biocompatible, bioresorbable fibers which include a natural material or an analog thereof; preferably polymeric in structure, which can provide mechanical strength and protection and lubrication while encouraging tissue ingrowth (e.g., collagen, reticulin, elastin, cellulose, or biosynthetic analogs thereof). These fibers may be ordered in substantially circumferentially-extending or substantially radially-extending orientations, with the density of fibers being substantially uniform throughout the matrix. Alternatively, the matrix fibers may be unordered. In either the ordered or unordered configuration, the density of the fibers may be non-uniform. In the non-uniform configuration, relatively high densities of fibers may be established at anticipated points of high stress by local application.

In an alternative aspect of the invention, the intrafibrillary and interfibrillary space is relatively high, a condition which promotes ingrowth of regenerated meniscal tissue. For example, the density of the meniscus may be in the range of about 10-25 g matrix/cm$^3$. Alternatively, the intrafibrillary and interfibrillary space is relatively low, a condition which provides cushioning, lubrication, and mechanical support for the knee joint and which retards tissue and cell ingrowth, thereby diminishing the rate of scaffold resorption (e.g., density is in the range of about 2-10 g matrix/cm$^3$).

The temporary stability of the shape of the structure when in vivo, and the rate of meniscal resorption, are both attributed to the effective crosslinking formation between at least one portion of the fibers. The crosslinking reagents used may be any biocompatible bifunctional reagents which interacts with amino groups, carboxyl, or hydroxyl groups on a single fiber (intramolecular crosslinks), or the fibers or on the fibers and the GAGs, resulting in covalent bond formation between adjacent molecules (intermolecular crosslinks). Useful cross-linking reagents include aldehydes, hexamethylene diisocyanate, bis-imidates, polyglycerol polyglycidyl ether, and carbodiimides.

The crosslinked device maintains sufficient degree of hydrophilicity and elasticity which simulates the properties of the natural meniscus, i.e., ability to sustain mechanical stress and to protect and lubricate articular surfaces. In addition, the structure provides an ideal environment for cell infiltration and extracellular matrix synthesis and deposition resulting in regeneration of natural meniscal tissue.

GAGs may be dispersed throughout the fibers. Alternatively, they may act as intermolecular crosslinks between fibers. These GAG crosslinks are composed typically of at least one of the group of molecules consisting of chondroitin 4-sulfate, chondroitin 6-sulfate, keratin sulfate, dermatan sulfate, heparin sulfate, and hyaluronic acid. The dispersion of GAG crosslinks is preferably uniform, but may be more concentrated at anticipated points of high stress, typically at the distal regions 14 and 16, and less concentrated in the central region 12 (FIG. 1). In such configurations, the GAG concentration may be in the range of about 0-25% in the distal regions 14 and 16, and in the range of about 0-10% in the central region 12. However, when uniform, the dispersion of GAG throughout the prosthetic meniscus may be, for example, in the range of about 1-15%.

Intermolecular crosslinkages can also be established through a dehydrothermal process (heat and vacuum) which results in peptide bond formation between an epsilon amino group of lysine or hydroxylysine and a carboxyl group of aspartic or glutamic acid.

The crosslinked device has a relatively high thermal stability between about 55-85° C., preferably between about 65-75° C., for sufficient in vivo stability. This may be achieved through manipulation of the crosslinking conditions, including reagent concentration, temperature, pH, and time.

In a one embodiment the prosthetic meniscus is constructed mainly of Type I collagen fibers without GAG crosslinks. Type I collagen fibers may be obtained from the Achilles tendons of animals. However, the fibers may also be obtained from animal skin or from the skin or tendon of humans. The tissues are treated with a series of mechanical and chemical means to either totally remove the non-collagenous materials or reduce them to a minimal level. In the preferred processing steps, the tendon or skin is mechanically disintegrated into fine pieces useful for further processing. The disintegration may be achieved by grinding the tissue at liquid nitrogen temperature, or by cutting the tissue into small pieces with a sharp knife. In certain applications, the tendons are mechanically disintegrated along the fiber direction in order to maintain the length of the fibers for mechanical strength.

Salt extraction of tendon at neutral pH removes a small portion of the collagen molecules that are newly synthesized and have not yet been incorporated into the stable fibrils. Salt also removes some glycoproteins and proteoglycans that are associated with collagen through electrostatic interactions. Other salts such as KCl and the like can be used as a substitute for NaCl.

Lipids that are associated with the cell membranes or collagenous matrices may be removed by first extracting with detergents such as Triton X-100, followed by extracting with ether-ethanol mixtures. The concentration of Triton X-100 is usually about 2-4%, but is preferably about 3%. The preferred mixture of ether-ethanol is usually at about a 1:1 ratio (v/v). The period of extraction is usually from 8 hours to 96 hours, as is preferably from about 24 to 48 hours.

Further extraction may be accomplished by matrix swelling conducted at two extreme pHs. Both acidic and basic swelling weakens the non-covalent intermolecular interactions, thus facilitating the release of non-covalently attached glycoproteins, glycosaminoglycans (GAGs), and other non-collagenous molecules through the open pores of the collagenous matrices.

The swelling of matrix at alkaline pH is done by treating the collagen at high pH with $Ca(OH)_2$, NaOH, or the like, for a period of about 8-96 hours. Alkali extraction in the presence of triple-helical stabilizing salts such as $(CH_3)NCl$, $NH_3SO_4$, or the like reduces the potential risk of denaturation of the collagen. Alkali treatment dissociates the non-cross-linked glycoproteins and GAGs from the collagen matrices. The alkali also removed the residual lipids through saponification.

The acid swelling may be conducted at a low pH in the presence of acetic acid, HCl, or the like. Like the alkali treatment, the acid swelling removes non-crosslinked glycoproteins and GAGs.

The non-triple helical portions of the molecule (telopeptides) are involved in intermolecular crosslinking formation. They are weak antigens and are susceptible to attack by proteases, such as pepsin, trypsin, and the like. Prolonged digestion with such proteases dissociates the fibrils (fibers) into individual molecules. However, if the digestion process is properly controlled such that maximal telopeptides are removed without complete dissociation, the immunogenic properties of the fibrils can be reduced to a minimal level without compromising the mechanical strength. For example, to isolate molecular collagen, the digestion of skin or tendon with pepsin is usually conducted at an enzyme:collagen ratio of about 1:10 for about 24-96 hours at below room temperature. In comparison, fibrils may be obtained by limited pepsin digestion achieved at a ratio of about 1:100 (enzyme:collagen) for about 24-96 hours at 4° C.

Collagen fibers obtained according to this methodology are then used to fabricate the prosthetic meniscus of the present invention. However, it must be appreciated that collagen obtained from other sources, such as biosynthetically-produced collagen or analogs thereof —may also be used in the construction of the prosthetic meniscus.

In one embodiment, the prosthetic meniscus further includes an adhesion molecule or adhesive portion or analog thereof which is incorporated within the network of fibers, and which aids in meniscal tissue regeneration. Useful adhesion molecules include peptides such as fibronectin (see e.g., U.S. Pat. Nos. 4,589,881, 4,661,111 and 4,578,079), a portion of which can be conjugated to, for example, chondroitin sulfate.

The method of fabrication includes molding the collagen fibers into a predetermined shape using, for example, the mold forms described below in conjunction with FIGS. 6-8. The fibers may be placed randomly in the mold, or may be oriented in specific directions to achieve a meniscus having specific structure characteristics. Other components such as GAGs which may participate in the crosslinking reaction, can be mixed in with the fibers in a random or non-random fashion before the structure is subjected to various crosslinking and dehydrating procedures including various chemical and/or dehydrothermal methods. Adhesion molecules or adhesive fragments or analogs thereof may be added to the structure before the final drying step by soaking the structure in a solution containing that molecule, or by specifically coupling it to an existing fiber or crosslink. For example, the adhesion portion of fibronectin may be crosslinked to chondroitin sulfate at a concentration of 3 peptide molecules per molecule chondroitin sulfate by soaking the prosthetic meniscus in a 50 mg/ml solution thereof.

By following the processes described in the above examples set forth herein below, a prosthetic meniscus of the form shown in FIGS. 2 or 3 may be constructed having the characteristics listed below in TABLE 1.

TABLE 1

Physical Characteristics height A = 0.20-0.40 inches
angle B = 25-45 degrees
radius C = 0.5-2.0 inches
height D = 0.05-0.10 inches
Density = 0.07-0.5 g/cm$^3$
Intra- and Interfibrillary space = 2-25 cm$^3$/g matrix Constituents fiber (collagen) content = 75-100%
GAG content = 0-25%

The following non-limiting examples describe methods of fabrication and in vivo testing of the prosthetic meniscus of the invention.

EXAMPLE 1

Mold Fabrication

A mold 100 useful for fabricating the prosthetic meniscus is made of implantable stainless steel or biocompatible plastics such as teflon, polypropylene, delrin, or combination of these materials. The mold 100 is composed of three pieces 102, 104, and 106 as shown in FIGS. 6-8.

Figure 6:
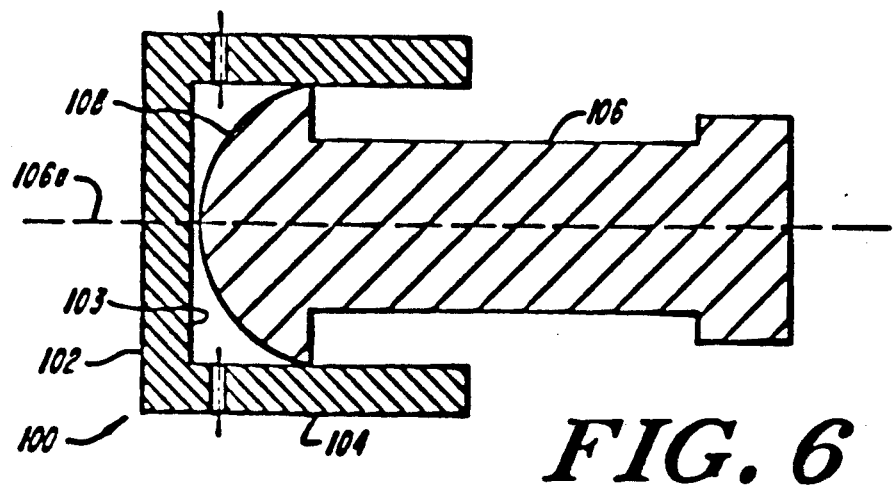
FIG. 6 shows a mold designed for the fabrication of a prosthetic meniscus having a cylindrical pad shape.

By way of example for the disk-shaped meniscus illustrated in FIGS. 4 and 5, the mold 100 of FIG. 6 is used. The first piece 102 is disk-like and has a diameter substantially equal to that of the desired meniscus. Piece 102 is perforated to allow liquid to pass through under pressure. The inner surface 103 of piece 102 has the desired shape of one side of the meniscus-to-be-formed.

The second piece 104 is a hollow cylinder which has the same inner dimension as the first piece 102. The third piece 106 is a cylindrical piston which has an outer diameter slightly less than the inner diameter of piece 104. The "top", or crown, surface 108 of piston 106 has the desired shape of one side of the meniscus-to-be-formed.

Figure 3:
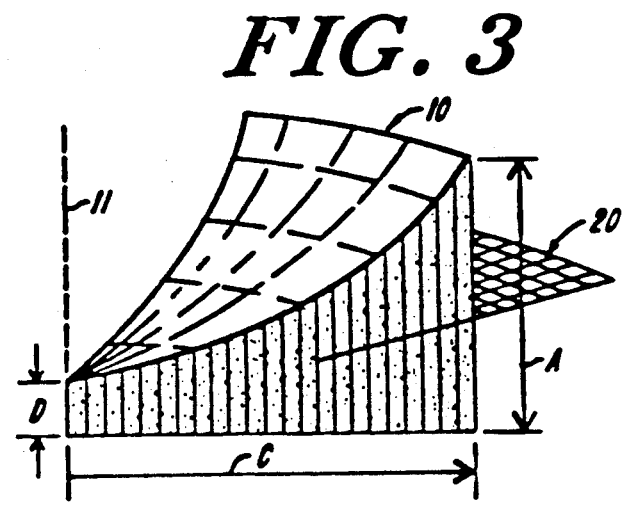
FIG. 3 shows a perspective radial section of the prosthetic meniscus of FIG. 2.
Figure 7:
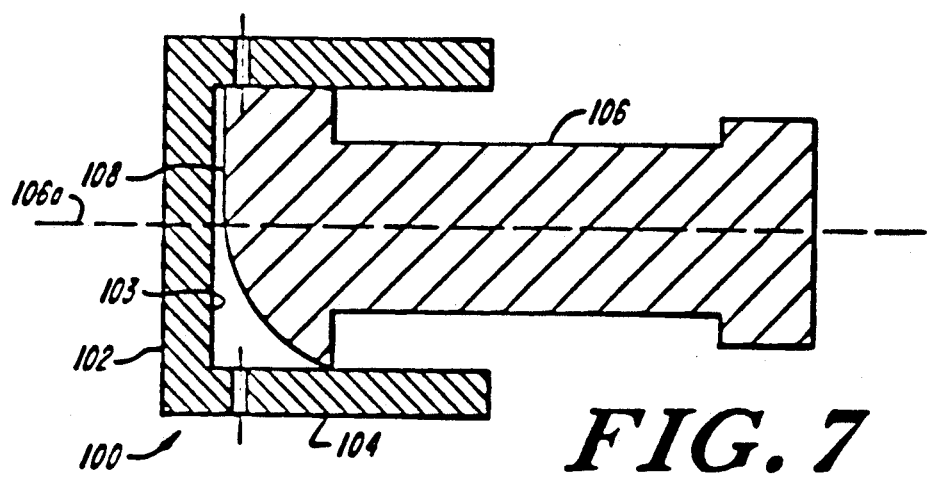
FIG. 7 shows a mold designed for the fabrication of a prosthetic meniscus having a crescent-shaped wedge form.

For the meniscus of FIG. 3, the mold of FIG. 7 is used where the shape of piece 102, and cross-section of piece 104 have the shape of an angular segment. For a flat circular disk meniscus, the mold 100 of FIG. 8 is used where pieces 102 and 104 are the same as in FIG. 6 and piece 106 is similar to that piece in FIG. 108 but has a flat crown surface 108.

Figure 8:
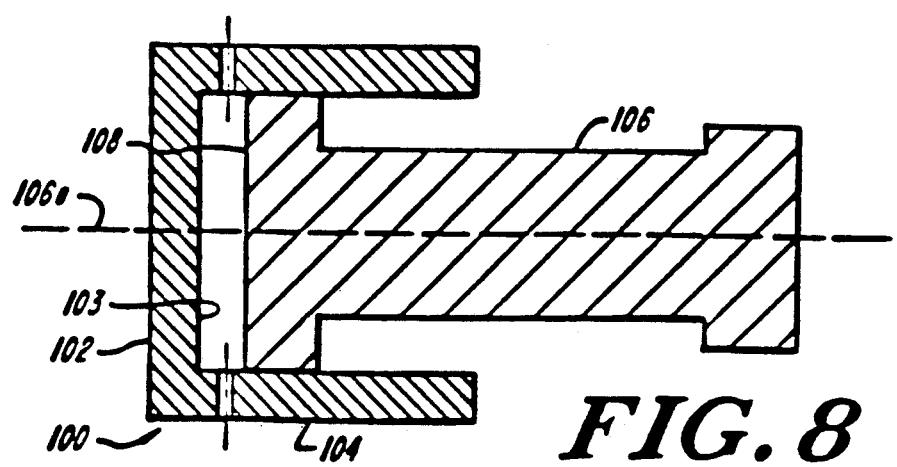
FIG. 8 shows a mold designed for the fabrication of a cylindrical prosthetic meniscus.

During fabrication of the meniscus 10, the piece 102 is first assembled within piece 104, as shown in FIGS. 6-8. The constituent fibers (in a fluid) are placed against the surface 103 of piece 102. Then the crown surface 108 of piston 106 is driven toward surface 103 along a compression axis 106a until the fibers are compressed, the fluid is driven out through piece 102, and the desired axial dimension of the compressed fiber array is attained. The mold is then frozen in preparation for chemical crosslinking.

EXAMPLE 2

Preparation of Purified Type I Collagen

A) Tissue

Bovine, porcine, or sheep Achilles tendon is obtained from USDA-approved slaughter houses. The preferred age of the animals is between 12-18 months. The tissue is kept cold during the purification process except where specified to minimize bacteria contamination and tissue degradation.

B) Mechanical Disintegration

The adhering tissues of carefully selected tendons are first scrapped off mechanically. The tendons are then minced or cut into fine pieces and washed in excess quantities (10 volumes) of cold water to remove residual blood proteins and water soluble materials.

C) Salt Extraction

The washed tendons are extracted in ten volumes of 5% NaCl, 0.01M Tris, pH 7.4, for 24 (+/−4) hours to remove salt soluble materials. The salt extracted tendons are repeatedly washed in about 10 volumes of water to remove the salt.

D) Lipid Extraction

The material is extracted in 3% Triton X-100 for 24 (+/−2) hours. The detergent is removed by extensive washing with water. The material is then extracted in 3-4 volumes of ether-ethanol (1:1 vol/vol) for 24 (+/−2) hours to further minimize the lipid content. The lipid extracted material is extensively washed in water to remove the ether and ethanol.

E) Matrix Swelling

The material is then subjected to two extreme pH extractions to remove non-collagenous materials. Alkaline extraction is conducted with 3-4 volumes of 0.2M NaOH at pH 12.5-13.5 at room temperature (RT) in the presence of 1.0M (CH)NCl for 24 (+/−2) hours with mild agitation.

Following alkaline extraction, the pH is neutralized with HCl and the material is washed with water. The pH is then adjusted to 2.5-3.0 by adding concentrated acetic acid to a final concentration of 0.5M. The acid extraction is continued for 24 (+/−2) hours with agitation.

F) Limited Proteolytic Digestion

The acid swollen tendon is then subjected to a limited proteolytic digestion with pepsin (enzyme: collagen = 1:100) for 24 (+/−) 2 hours. The pepsin and telopeptides are removed through dialysis.

The swollen fibrillar material is then coacervated by adjusting the pH to its isoionic point with 1M NaOH or HCl or by adjusting the ionic strength to 0.7 with NaCl. The aggregated collagen fibers are harvested by filtration, and the filtered material extensively washed with cold buffered solution. The highly purified type I collagen may be stored ($-20°$ to $-40°$ C.) until used.

EXAMPLE 3

Device I Fabrication

A) The collagen content of the highly purified type I collagen fibrils from EXAMPLE 2 is determined either by gravimetric methods or by determining the hydroxyproline content assuming a 13.5% by weight of hydroxyproline in type I collagen. The amount of purified material needed to fabricate a given density of a meniscus device is then determined and weighed.

B) A solution of fibrillar collagen is carefully fit into a mold of specified dimensions, e.g. according to the exemplary meniscus described above in conjunction with FIGS. 2-5 (see EXAMPLE 1 and FIGS. 6-8 for the description of molds). Collagen fibers are laid down in random manner or in an oriented manner. In the oriented manner, circumferential orientation of the fibers is produced by rotation of the piston about its principal axis as the material is compressed in the mold; radial orientation is produced by manual painting of the collagen fibers in a linear, radially directed fashion.

C) The fibers are frozen at $-20°$ C., turned out of the mold, and thawed at RT.

D) The fibers are then resuspended in phosphate buffered saline, put back into the mold in the desired orientation(s), and compressed with the piston.

E) The compressed fibers are then refrozen at $-20°$ C. and then thawed at RT.

F) The resulting structure is crosslinked by soaking in a 0.2% glutaraldehyde solution, pH 7.6, for 24 ($+/-0.5$ hours). Each glutaraldehyde-cross-linked meniscal device is subsequently rinsed repeatedly in 500 ml of phosphate buffered saline (PBS) solution, pH 7.4, for 4, 8, 24 and 48 hours.

G) the rinsed matrix is then lyophilized.

EXAMPLE 4

Device II Fabrication

A)-G) (same as in EXAMPLE 3)

H) The lyophilized matrix is subjected to dehydrothermal crosslinking by vacuum and heat. The vacuum is first applied to reduce the residual water content to a minimal level (some structural water, about 3%, may still be associated with collagen triple-helix as part of the structure stabilizing factor). The heat is increasing in steps to 110° C. ($+/-5°$), and continually applied at 110° C. under vacuum for 24 ($+/-2$) hours.

EXAMPLE 5

Device III Fabrication

A) (same as in EXAMPLE 3)

B) The collagen material is dispersed in 0.01M HCl solution at pH 2-2.5. Predetermined amounts of various GAGs are weighed and dissolved in water. For example, for a given density of 0.25 g/cm, the collagen content will be 0.244 g, the hyaluronic acid content will be 0.003 g, and the chondroitin sulfate content will be 0.003 g for a 2.5% GAG content. The GAG solution is mixed in with the collagen solution and placed in the mold in the desired orientation as described in EXAMPLE 2.

C)-G) (same as in EXAMPLE 3)

EXAMPLE 6

Device IV Fabrication

A)-C) (same as in EXAMPLE 3)

D) (same as in EXAMPLE 3 except that the fibers laid down are not compressed.

E)-G) (same as in EXAMPLE 3)

EXAMPLE 7

Device V Fabrication

A)-E) (same as in EXAMPLE 3)

F) The molded collagen is crosslinked in 5%, polyglycerol polyglycidyl ether in 50% ethanol and 0.1M $Na_2CO_3$ at pH 10.0 for 24 ($+/-2$) hours. The crosslinked device is rinsed for 4, 8, 24 and 48 hours, each with 500 ml of PBS, pH 7.4.

G) (same as in EXAMPLE 3)

EXAMPLE 8

Device VI Fabrication

A)-E) (same as in EXAMPLE 3)

F) The molded collagen is crosslinked in the presence of 1-ethyl-3-(3-dimethylaminopropyl) carbodiimide (10 mg/g matrix) in 0.9% NaCl, pH 4.7 at room temperature for 24 ($+/-2$) hours. The addition of carbodiimide is made every 3-4 hours, and the pH is adjusted to 4.7 after each addition of carbodiimide.

G) (same as in EXAMPLE 3)

EXAMPLE 9

Device VII Fabrication (A)-(D) same as steps (A)-(D) as described in Example II.

(E) For attachment purposes, a mesh of absorbable polyglyconate suture material, matched to the size of the mold, is laid in the dispersed collagen such that it protrudes from the structure's periphery to form a skirt which may extend over the tibial plateau. This mesh provides both immediate attachment sites and long term fibrous ingrowth.

EXAMPLE 10

Testing

The prosthetic menisci were evaluated in vivo using animal models and in vitro to determine ability to function or to serve as a regeneration template for normal meniscal tissues.

1. In vivo Studies

Seventeen prosthetic menisci (device III type) were implanted into eleven immature Yorkshire pigs. Seven joints underwent a two-thirds subtotal resection of the medial meniscus with replacement by a matched prosthetic meniscus; two joints underwent a two-thirds subtotal resection alone; two joints received a similar subtotal meniscectomy with the resected portion immediately replaced with suture fixation; and two joints received total meniscectomy alone.

Figure 9:
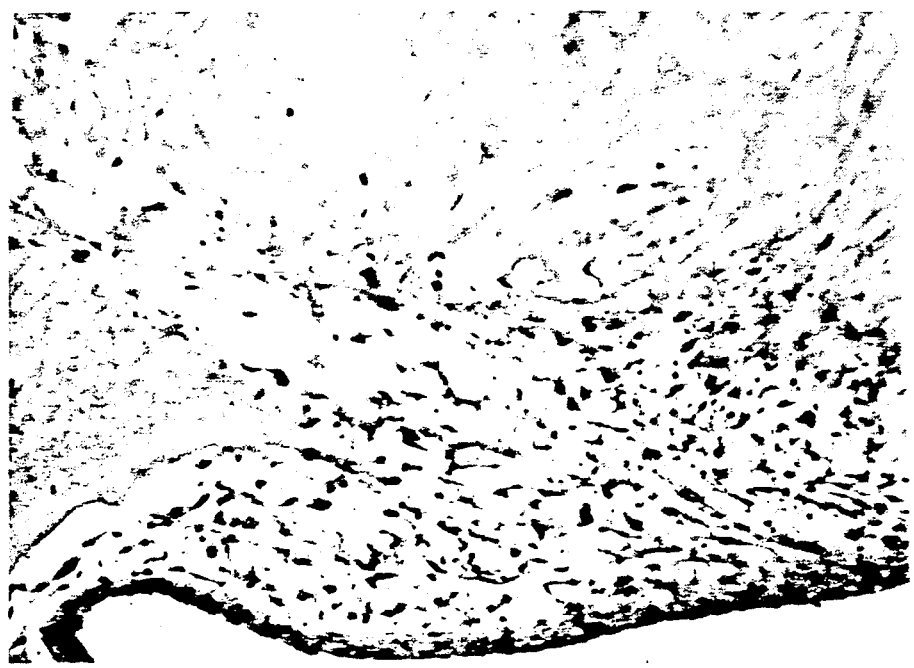
FIG. 9 is a photographic representation of in vivo meniscal regrowth after 80% resection and implantation of the prosthetic meniscus.

Evaluation of all joints was made at 3 or 6 weeks. All arthrotomies healed well, and all animals progressed to full weight bearing. At final evaluation all prosthetic material had been partially or completely resorbed without evidence of joint destruction or cartilage abrasion. Neovascularization was observed as the basic healing mechanism in both the prosthetic implanted menisci as well as in the controls, and in all joints there was evidence of early meniscal regeneration. The prosthetic meniscus material conformed to the appropriate joint shape. In addition, there was no clinical evidence of implant rejection over a 6 week period. Histologically, there was acute inflammation followed by neovascularization and extensive fibroplasia with early hyalinization of the newly formed collagen. (See FIG. 9)

In vivo studies of the invention in mature dogs have demonstrated induced meniscal regeneration through the prosthetic material. Normally, the mature canine stifle is known to not regenerate a meniscus and is known to develop significant arthritic changes. However, six weeks after meniscectomy and implantation of scaffolds in accordance with the present invention, there occurred significant regeneration of the meniscus through the scaffolds. The scaffolds provided joint protection, as determined by diminished cartilage erosions, osteophyte formation and affinity for India ink.

Figure 11:
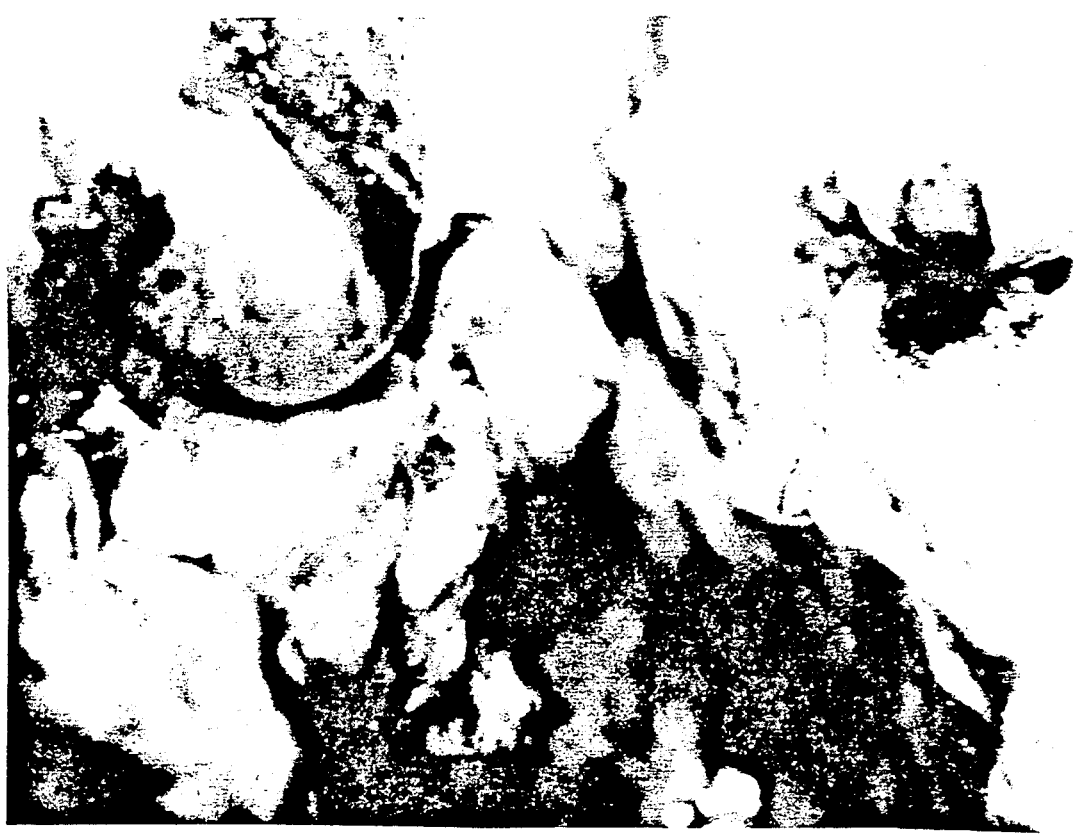
FIG. 11 is a photographic representation of two canine knee joints three months after surgical resection.
Figure 12A:
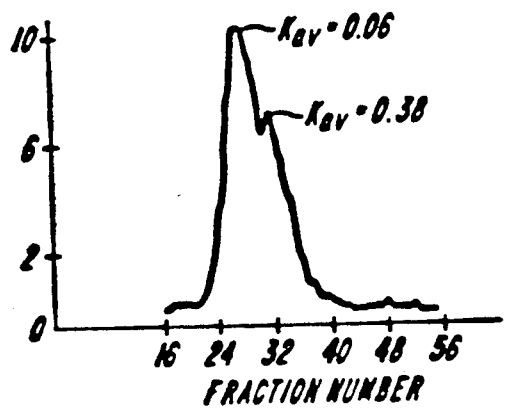
FIG. 12A-D is a graph showing the hydrodynamic profiles of the proteoglycan aggregates in the regenerated meniscus compared to the resected rim alone.
Figure 12B:
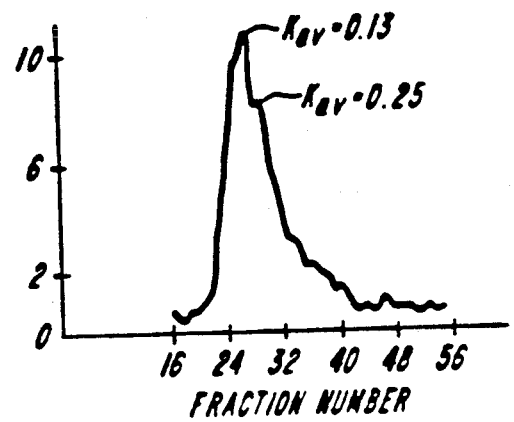
Figure 12C:
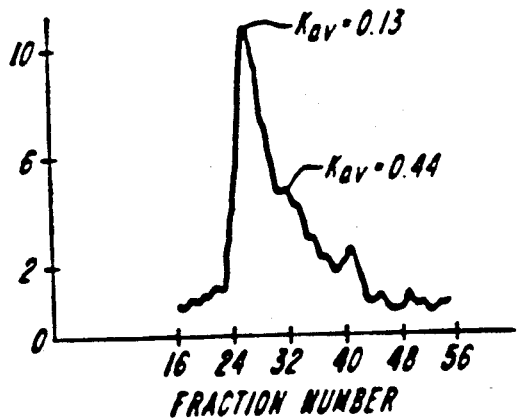
Figure 12D:
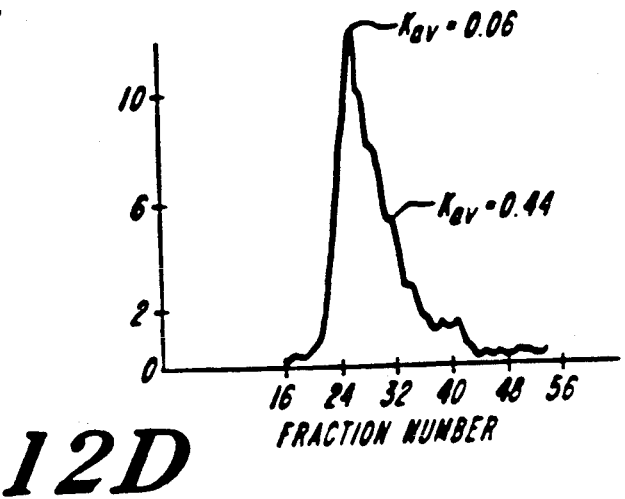

FIG. 11 is a photographic representation of two canine knee joints three months after surgical resection. The joints were protected by the prosthetic implant with subsequent regrowth of a new meniscus. The joint on the right in FIG. 11 underwent an 80% meniscal resection alone. The dramatic articular cartilage protection is highlighted by India ink.

New collagen and glycosaminoglycan formation was evidenced histologically, by Alcian Blue and Masson's Trichrome stains. The cells which populated the meniscal regeneration template synthesized less proteoglycan per gram net weight of tissue than did the remaining fibrochondrocytes of the resected meniscal rim remnant when measured by radio sulphate incorporation (ratio 1:8). However, the proteoglycans synthesized within the implant were stabilized in the matrix based on extractability with guanidine hydrochloride (ratio 1:8). The hydrodynamic size and chromatographic profiles of the proteoglycans synthesized within both the meniscal implants and the meniscal remnants were similar when analyzed on a Sephacryl S-500 column.

FIG. 12 is a graph showing the hydrodynamic profiles of the proteoglycan aggregates in the regenerated meniscus compared to the resected rim alone.

2. In vitro Studies

Menisci were aseptically harvested from mature dogs, trimmed of all adherent tissue, and placed into Gey's balanced saline solution. Each meniscus was bisected in the coronal plane and 3 mm full-thickness circular defects were made in each meniscal half. The defects were filled with a 3 mm diameter plug of one of two prototypes of a complex collagen-based biosynthetic scaffold (prosthetic meniscus). The menisci were placed in six well culture plates containing six ml of Dulbecco's modified Eagle's medium supplemented with 10% fetal bovine serum, sodium ascorbate, and 0.1% penicillin/streptomycin. Cultures were maintained at 37° C. in a humidified atmosphere of 10% $CO_2$/90% air, fed three times per week, and placed in fresh culture wells every week to prevent the formation of explant cell cultures. At intervals of one, four, and six weeks after initiation of culture, three menisci from each group were removed, fixed, and evaluated with serial sections and staining.

Figure 10:
FIG. 10 is a photographic representation of an explanted canine meniscus containing a section of scaffold, and demonstrating in vitro regrowth of meniscal tissues into the scaffold.

The results (shown in FIG. 10) demonstrated increasing cellular migration and invasion over time. There was no apparent toxicity from the material. The morphologic characteristics of the migrating cells were more fusiform and elongated than native fibrochondrocytes. The depth of cellular penetration into the scaffold appeared to be limited by the density of the prosthetic complex.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of regenerating meniscal tissue in vivo comprising the steps of:
    (a) fabricating a prosthetic menisucs comprising a dry porous matrix of biocompatible and bioresorbable fibers, said fibers selected from the group consisting of natural polymers, and analogs, and mixtures thereof,
    said matrix being adapted to have in vivo and outer surface contour substantially the same as that of a natural meniscus,
    said matrix having pore size in the approximate range of greater than 50 microns to less than about 500 microns,
    whereby said matrix establishes an at least partially bioresorbable scaffold adapted for ingrowth of meniscal fibrochondrocytes, and wherein said scaffold and said ingrown meniscal fibrochondrocytes support natural meniscal load forces; and
    (b) implanting said prosthetic meniscus into a knee joint by surgical procedure.

2. The method of claim 1 wherein said fabricating step includes crosslinking at least a portion of said fibers.

3. The method of claim 1 wherein said prosthetic meniscus fabricated in step (a) comprises a plurality of glycosaminoglycan molecules.

4. The method of claim 1 wherein said prosthetic meniscus fabricated in step (a) assumes the shape of a native meniscus when implanted in step (b).

5. The method of claim 5 wherein said fabricating step includes fabricating a prosthetic meniscus comprising a mesh extending from portions of the outer surface of said matrix, said mesh being resorbable and biocompatible.

* * * * *